US010111693B2

(12) United States Patent
P et al.

(10) Patent No.: US 10,111,693 B2
(45) Date of Patent: Oct. 30, 2018

(54) ORTHOPEDIC EXTERNAL COMPRESSION PLATE

(71) Applicants: Kannan P, Sivaganga (IN); S. Swarna, Sivaganga (IN)

(72) Inventors: Kannan P, Sivaganga (IN); S. Swarna, Sivaganga (IN)

(*) Notice: Subject to any disclaimer, the term of this patent is extended or adjusted under 35 U.S.C. 154(b) by 527 days.

(21) Appl. No.: 14/434,099

(22) PCT Filed: Oct. 4, 2013

(86) PCT No.: PCT/IB2013/059114
§ 371 (c)(1),
(2) Date: Apr. 8, 2015

(87) PCT Pub. No.: WO2014/057405
PCT Pub. Date: Apr. 17, 2014

(65) Prior Publication Data
US 2015/0250509 A1 Sep. 10, 2015

(30) Foreign Application Priority Data
Oct. 8, 2012 (IN) .......................... 4191/CHE/2012

(51) Int. Cl.
*A61B 17/80* (2006.01)
(52) U.S. Cl.
CPC ...... *A61B 17/8014* (2013.01); *A61B 17/8004* (2013.01); *A61B 17/8009* (2013.01)
(58) Field of Classification Search
CPC .................. A61B 17/8004–17/8019
See application file for complete search history.

(56) References Cited

U.S. PATENT DOCUMENTS

| 3,244,170 A * | 4/1966 | McElvenny | A61B 17/7225 606/105 |
| 3,386,437 A * | 6/1968 | Treace | A61B 17/8019 254/126 |
| 3,400,711 A * | 9/1968 | Frick | A61B 17/8019 29/238 |
| 3,866,607 A * | 2/1975 | Forsythe | A61B 17/8019 606/105 |

(Continued)

FOREIGN PATENT DOCUMENTS

WO   WO-2011006228 A1 * 1/2011 ......... A61B 17/8028

*Primary Examiner* — Kristen Matter (57) ABSTRACT

The present invention provides an orthopedic external compression unit having a locking plate unit and a method for locking and compressing the fractured bones without contact and friction between plate and bone, wherein the locking plate unit comprises of a locking plate, an external apparatus and a holder, wherein the locking plate includes plurality locking holes and at least an elongated hole, wherein the holder is placed at the elongated hole. The holder is configured to hold the locking plate above the bone for enabling to make required movement of locking plate in horizontal direction. Accordingly, fastening the compressing unit using a non-locking screw to the plate converts the vertical movement of head-screw into horizontal movement of connecting rod of the compression unit, thereby enabling to move the plate along with one end of fractured bone towards the fractured site thus producing compression between the fractured bones.

9 Claims, 7 Drawing Sheets

(56) References Cited

U.S. PATENT DOCUMENTS

| | | | | |
|---|---|---|---|---|
| 4,929,247 A | * | 5/1990 | Rayhack | A61B 17/8019 606/105 |
| 2001/0047172 A1 | * | 11/2001 | Foley | A61B 17/1728 606/86 B |

* cited by examiner

ORTHOPEDIC EXTERNAL COMPRESSION PLATE

FIELD OF INVENTION

The embodiments herein generally relate to medical devices in orthopedic, more specifically, it relates to a bone locking plate and bone locking plate unit for fixation of parts of fractured bone, particularly connecting and compressing the fractured bone without direct contact and friction between the locking plate unit and bone.

BACKGROUND OF THE INVENTION

Plating of bones is a time tested principle which has evolved from bridging the fractured bone using round holed plate, wherein normal screws are used to press the plate to the bone for holding the fractured bone together while the bone gets healed. The usage of bone plates had revolutionized the trend towards the surgical approach of bone fractures. However, conventional plates could not produce compression between the fractured bones and also led to compromise of periosteal blood supply.

To overcome the problem associated with the convention plate, dynamic compression plates have been developed with oval holes with a slope. The slope of the hole is inclined at an angle and tightening of a screw-head towards the hole converts the vertical movement of screw-head into horizontal movement of plate thus producing compression between the fractured bones. However, the compression of bones results from friction between bone and undersurface of the plate, which leads to reduction of periosteal blood supply to bone thus weakens and erodes the bone.

Subsequently, limited contact plates had been developed to minimize the contact between plate and bone by providing undercuts to enable limited contact and lower the erosion of bone, however the problem of friction could not be completely eradicated.

The usage of dynamic compression plates and limited contact plates results in friction between plate and bone, hence even a small spot of weakness can defeat the stability. Moreover, the plate may loosen and fail in rigidity, which can also predispose to infection.

Thus to eliminate the above friction phenomena, locking plates have been introduced which are non-contact plates and does not contact the bone underneath once the screw is locked. In such locking plate, threads were provided at holes and heads of screw with matching pitch for achieving non-contact with bones and also providing structural rigidity, strength and stability. On the other hand, the locking plates could not compress the fracture site and nonunion of bones can occur when there is an unreduced fracture.

In order to overcome the problem associated with the prior art, research has been focused towards developing a locking plate which can combine the locking and compression principles to form a single hole pairing both of them in a shape like peanut shell or otherwise. Such type of locking plate with locking screws and compression screws can offer both the locking and compressing of bones and buttressing option all in one. However, it has been observed that the locking screw can only provide non-contact on bone surface, but tightening of the compression screw resulted in contact with bone and also friction between bone and locking plate while compressing.

Therefore there exist a need in the art to develop a method and novel design of locking plate and locking plate unit to overcome the problem associated with the prior art, and also provide exclusive non-contact plate which can achieve locking and compression without friction and contact between bone and plate interface.

OBJECTS OF THE INVENTION

Some of the objects of the present disclosure are described herein below:

A main object of the present invention is to provide a locking plate unit for locking and compressing the fractured bone, wherein in the locking plate unit is made of metal, alloy, polymer, bio-absorbable material or combination of them.

Another object of the present invention is to provide a locking plate unit for locking and compressing the fractured bone without friction and contact between plate and bone.

Still another object of the present invention is to provide a locking plate comprises plurality of circular locking holes and at least an elongated hole.

Yet another object of the present invention is to provide an external apparatus comprising a fixing unit, a compression unit and a box for compressing the fractured bone.

Another object of the present invention is to provide a holder in the elongated hole for holding the locking plate above the bone for enabling to make required movement of locking plate in horizontal direction.

Another object of the present invention is to provide a method for locking and compressing the fractured bone using the locking plate unit.

The other objects and advantages of the present invention will be apparent from the following description when read in conjunction with the accompanying drawings which are incorporated for illustration of preferred embodiments of the present invention and are not intended to limit the scope thereof.

SUMMARY OF THE INVENTION

In view of the foregoing, an embodiment herein discloses a locking plate unit and a method for locking and compressing the fractured bones. Accordingly, the locking plate unit comprises a locking plate, an external apparatus and a holder, wherein the locking plate includes a plurality of circular locking holes and at least an elongated hole, wherein the elongated hole is preferably provided in at least one side of the locking plate, wherein the holder is placed at the elongated hole. In an embodiment, the external apparatus includes a compression unit, a fixing unit and a box, wherein the box includes two racks, a gear mechanism placed in between the two racks and two supporting members to hold the racks with the gear mechanism, wherein the compression unit is connected to a rack through a connecting rod and fixing unit is connected to another rack through another connecting rod. In an embodiment, the locking plate unit is made of metal, alloy, polymer, bio-absorbable material or combination of them. Optionally, the bottom surface of compression unit and fixing unit is coated with polymer to avoid friction damages. In a preferred embodiment, the holder is configured to hold the locking plate above the bone for enabling to make required movement of locking plate in horizontal direction. Further the holder is internally configured to allow a drill bit or tap and lock the drill bit or tap's graduations. Further, the holder enables to hold and allow the locking plate to move only in the horizontal direction but restrict vertical movement. In an exemplary embodiment, the holder is provided in a shape like dumb bell with a hole throughout its length at centre for allowing the drill bit or tap, and also a slit at outer surface is provided longitudinally throughout its radius for facilitating press fit and release.

In an embodiment, the compression unit includes a slope at predetermined variable angle for receiving a hemispherical head screw for fastening the compressing unit using a non-locking screw to the locking plate to convert a vertical movement of screw head into horizontal movement of connecting rod of the compression unit, which in turn results in opposite direction movement of another connecting rod of the fixing unit, thereby enabling to move the locking plate along with one end of fractured bone towards the fractured site thus producing compression between the fractured bones.

According to an embodiment, a method for locking and compressing fractured bone using a locking plate unit is provided, wherein the method comprising the step of fastening the locking plate to one side of fractured bone using at least a locking screw for keeping the locking plate over bone in a non-contact way, drilling a graduated drill bit or tap at predetermined position in an elongated hole provided in the locking plate, placing a holder in the elongated hole over the drill bit or tap for holding and allowing the locking plate to move only in the horizontal direction, wherein the holder is internally configured to hold with the drill bit or tap and to lock the drill bit or tap or is stabilized by external means, placing a fixing unit on the locking plate near the locked screw side, fastening the fixing unit with the locking plate using a locking screw having threads matching the threads of hole, placing a compression unit on the locking plate near the locked screw side, providing a box includes two racks, a gear mechanism placed in between the two racks and two supporting members to hold the racks with the gear mechanism, connecting the compression unit to a one of the racks through a connecting rod, and connecting fixing unit to another rack through another connecting rod, wherein the compression unit includes a slope at predetermined variable angle for receiving a hemispherical screw head for fastening the compressing unit using a non-locking screw to the locking plate to convert a vertical movement of headscrew into horizontal movement of connecting rod of the compression unit, which in turn results in opposite direction movement of another connecting rod of the fixing unit, thereby enabling to move the locking plate along with one end of fractured bone towards the fractured site, wherein the bone is connected and compressed without having direct contact or friction with locking plate.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The detailed description is set forth with reference to the accompanying figures. In the figures the use of the same reference numbers in different figures indicates similar or identical items.

DETAILED DESCRIPTION OF THE PREFERRED EMBODIMENTS

The embodiments herein and the various features and advantageous details thereof are explained more fully with reference to the non-limiting embodiments and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for developing a locking plate and locking plate unit for locking and compressing the fractured bone without friction and contact between bone and locking plate interface. The embodiments herein achieve this by providing a locking plate unit with an external compression unit for compressing the fractured bone, wherein the compression unit is temporarily fixed to the locking plate. Referring now to drawings, and more particularly to FIGS. 1 through 6, where similar reference characters denote corresponding features consistently throughout the figures, there are shown preferred embodiments.

Figure 1:
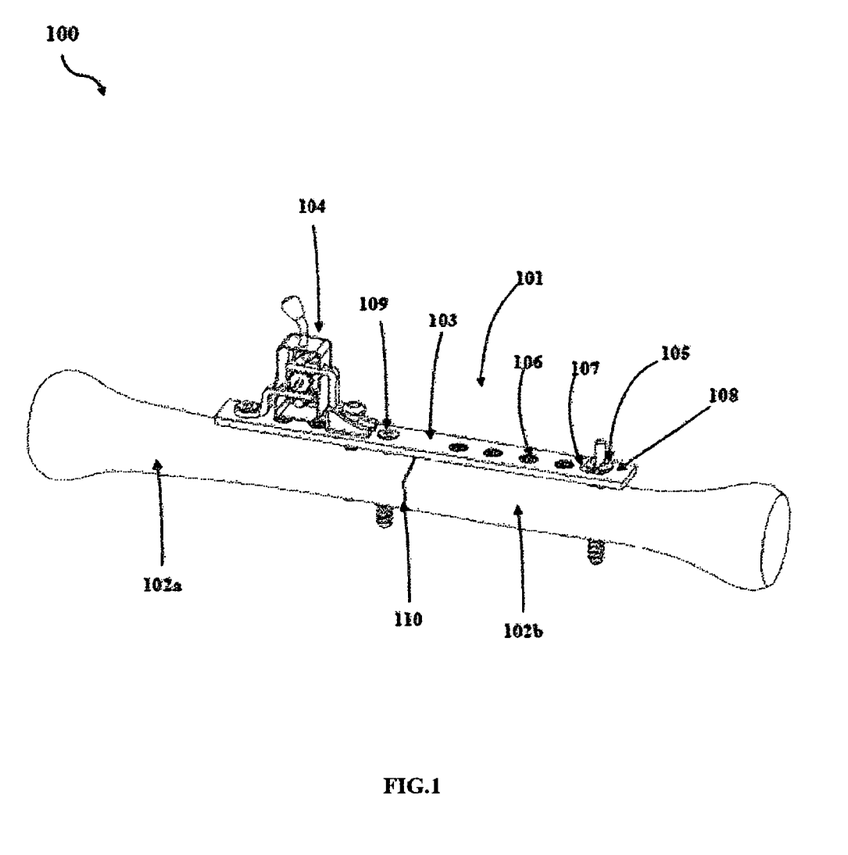
FIG. 1 illustrates a perspective view of a locking plate unit with fractured bone for locking and compressing the fractured bone, according to an embodiment herein.
Figure 2:
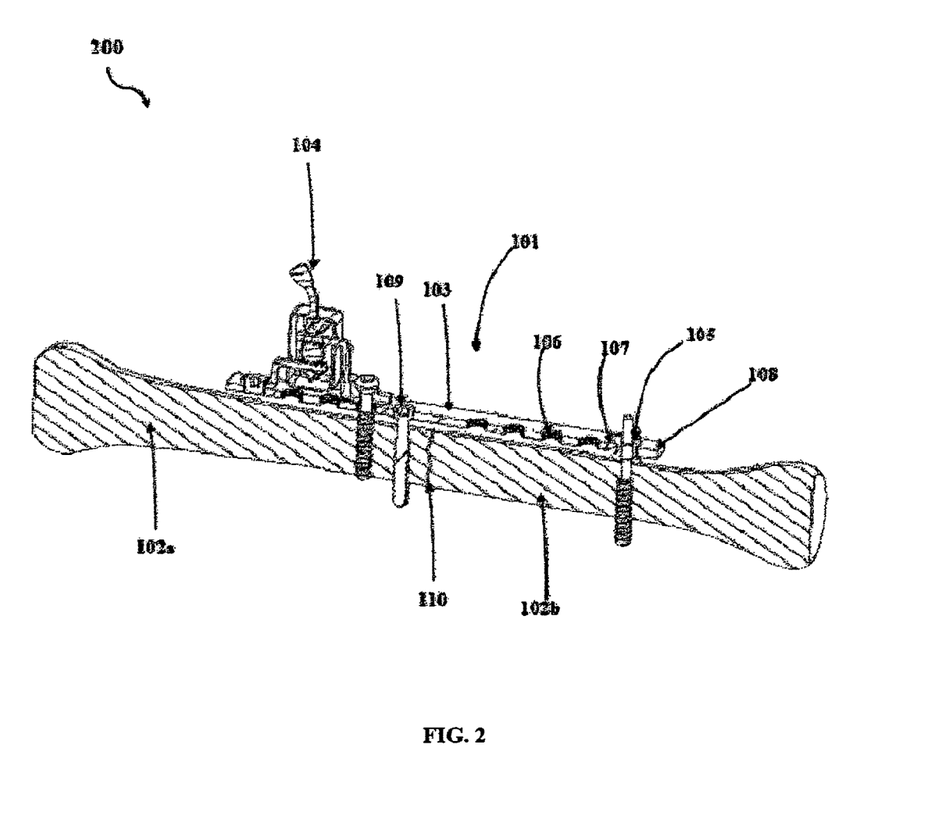
FIG. 2 illustrates a cross section view of the locking plate unit with fractured bone for locking and compressing the fractured bone, according to an embodiment herein.
Figure 3:
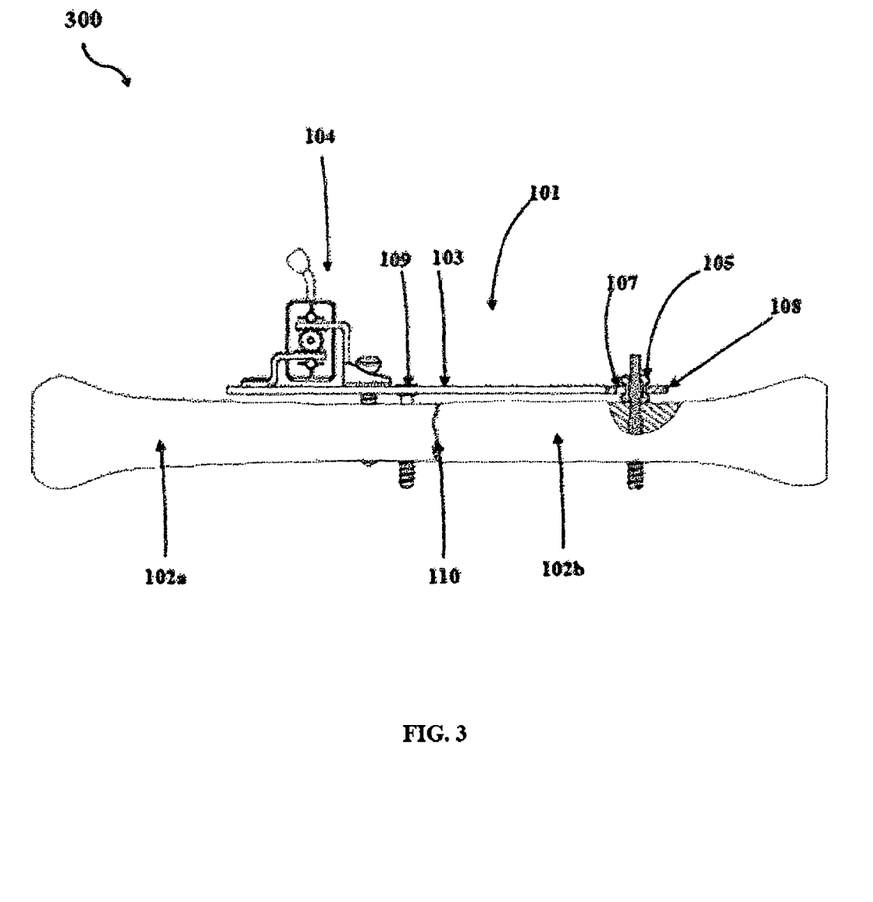
FIG. 3 illustrates a front view of the locking plate unit with fractured bone for locking and compressing the fractured bone, according to an embodiment herein.

According to an embodiment, FIG. 1 illustrates a perspective view 100 of a locking plate unit 101 with fractured bone 102 for locking and compressing the fractured bone 102. In an embodiment, a cross section view 200 of the locking plate unit 101 with fractured bone 102 is illustrated in FIG. 2, and a front view 300 of the locking plate unit 101 with fractured bone 102 is illustrated in FIG. 3. In an embodiment, the locking plate unit 101 comprises of a locking plate 103, an external apparatus 104 and a holder 105, wherein the locking plate unit 101 is made of metal, alloy, polymer, bio-absorbable material or combination of them. The locking plate 103 includes a plurality of circular locking holes 106 and at least an elongated hole 107. In an embodiment, the holder 105 is placed at the elongated hole 107 to hold the locking plate 103. In another embodiment, the holder 105 can be placed at circular locking holes 106 or the elongated hole 107 to hold the locking plate above the bone in non contact fashion. In a preferred embodiment, the elongated hole 107 is preferably provided in at least one end 108 of the locking plate 103. According to an embodiment, the holder can also be used in non locking holes if required.

In an embodiment, by placing the holder in circular locking holes 106 or elongated hole 107, the underlying fragment of bone can be controlled in horizontal plane movement such as compression, distraction or angulations using the drill bit or tap within the holder 105.

Figure 4:
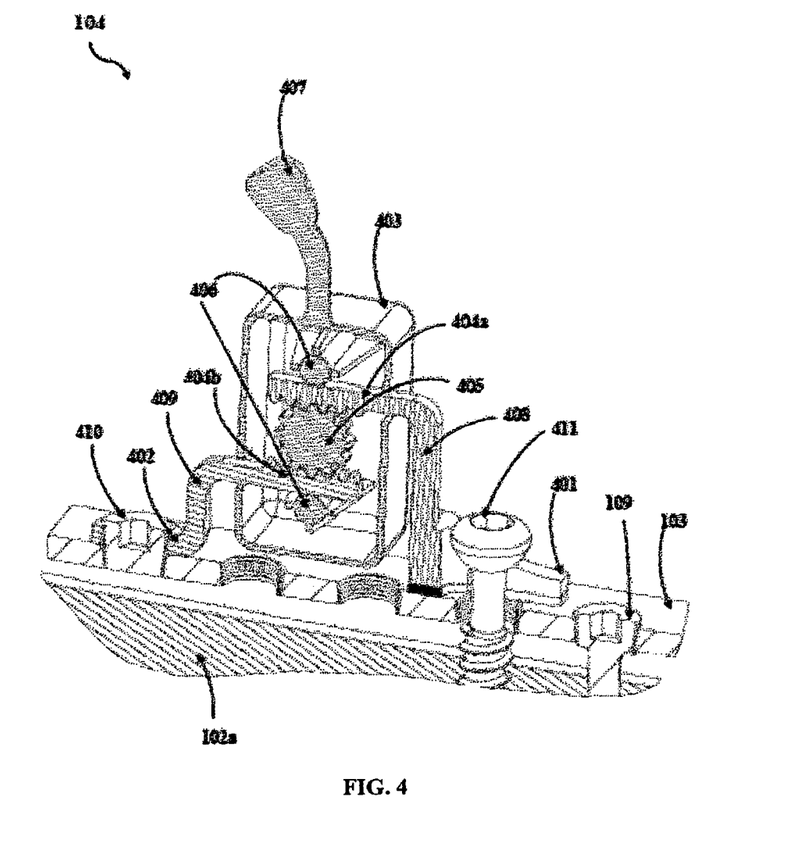
FIG. 4 illustrates an external apparatus includes a compression unit, a fixing unit and a box, according to an embodiment herein.

FIG. 4 illustrates an external apparatus 104 for temporarily fixing it with the locking plate 103, according to an embodiment. The external apparatus 104 can include a compression 401 unit, a fixing unit 402 and a box 403, wherein the compression unit 401 is temporarily fixed to the locking plate 103. In one embodiment, the box 403 can include two racks 404a, 404b, a gear mechanism 405 in between the two racks 404a, 404b and two supporting members 406 to hold the racks 404 with the gear mechanism 405. The box 403 can be provided with a handle 407 at the top to hold the box 403 in hand. Further, the box 403 can be provided with an upper and lower slot to allow the respective racks 404 to move inside box 403. Moreover, the box 403 can be configured to be in non-contact status with the locking plate 103.

According to one embodiment, the compression unit 401 is connected to the rack 404a through a connecting rod 408. In an embodiment, the compression unit 401 utilizes the two cylinder and sphere principle, but it is applied independently over the locking hole 106. A hemispherical head screw 411 is a non locking screw which cannot be locked with the locking plate 103 and provided above the compression unit 401 for fastening. Therefore, fastening the hemispherical head screw 411 can enable to move the compression unit 401 horizontally. In an embodiment, the hemispherical head screw 411 passes through a locking hole 106 and is inserted into the bone 102a. In another embodiment, the hemispherical head of screw 411 can be configured for fastening it without inserting inside the bone 102. For instance, a threaded rod bit having matching thread of locking hole at one end and also threaded with different pitch along its length can be provided and placed in between the compression unit 401 and tightened with the locking plate 103. Further, the hemispherical head of screw 411 may include cylindrical hole at the centre with matching thread to the rod bit is paired such that the head of screw 411 alone be inserted over the threaded rod so that upon fastening the hemispherical head part of screw 411 itself would enable a vertical movement of hemispherical head into the horizontal movement of the compression unit 401.

According to an embodiment, the fixing unit 402 with a locking slot is connected to another rack 404b through another connecting rod 409. Further, the fixing unit 402 is fastened with the locking plate 103 using a locking screw 410 with matching threads to the locking hole 106. Optionally, the locking screw 410 can be further fastened with the fractured bone 102 along with the locking plate 103. In an embodiment, the bottom surface of compression unit 401 and fixing unit 402 can be coated with polymer to avoid friction damages.

According to an embodiment, the compression unit 401 can be configured for temporarily connecting with the locking plate 103 without the external apparatus 104 for compression of fractured bone 102.

Figure 5A:
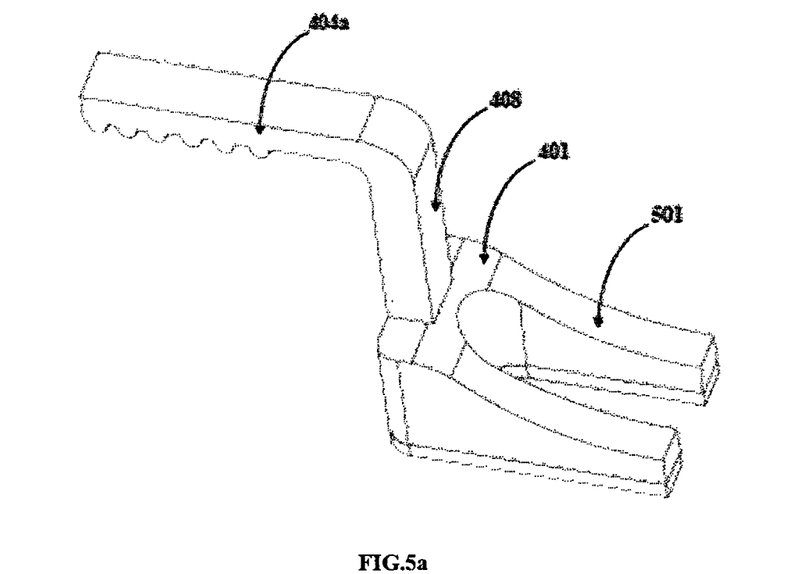
FIG. 5a illustrates side perspective view of a compression unit for compressing the fractured bone, according to an embodiment herein.
Figure 5B:
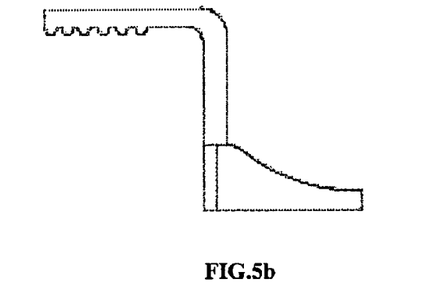
FIG. 5b illustrates side view of a compression unit for compressing the fractured bone, according to an embodiment herein.
Figure 5C:
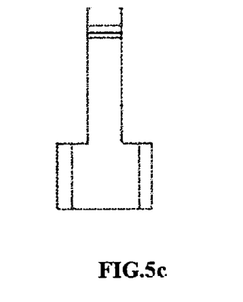
FIG. 5c illustrates top view of a compression unit for compressing the fractured bone, according to an embodiment herein.
Figure 5D:
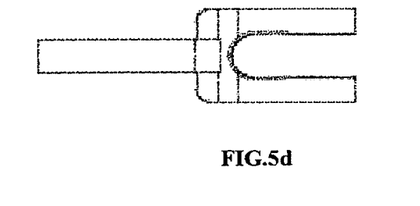
FIG. 5d illustrates front view of a compression unit for compressing the fractured bone, according to an embodiment herein.

FIG. 5a illustrates side perspective view of a compression unit 401 for compressing the fractured bone 102, according to an embodiment. FIG. 5b illustrates side view of a compression unit for compressing the fractured bone, according to an embodiment. FIG. 5c illustrates top view of a compression unit for compressing the fractured bone, according to an embodiment. FIG. 5d illustrates front view of a compression unit for compressing the fractured bone, according to an embodiment. Accordingly, the compression unit 401 includes a slope 501 at predetermined variable angle for receiving hemispherical head screw 411 for fastening the compressing unit 401 using a the hemispherical head screw 411 [non-locking screw] to the locking plate to convert a vertical movement of head-screw into the horizontal movement of connecting rod 408 of the compression unit 401.

Figure 6A:
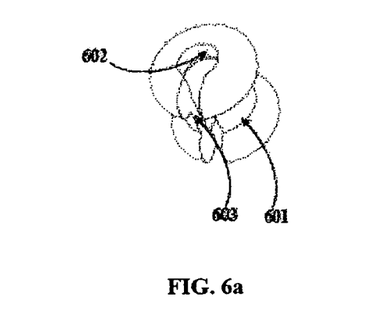
FIG. 6a illustrates a holder placed at an elongated hole provided in the locking plate to hold and allow the locking plate to move only in the horizontal direction and to restrict a vertical movement, according to an embodiment herein.
Figure 6B:
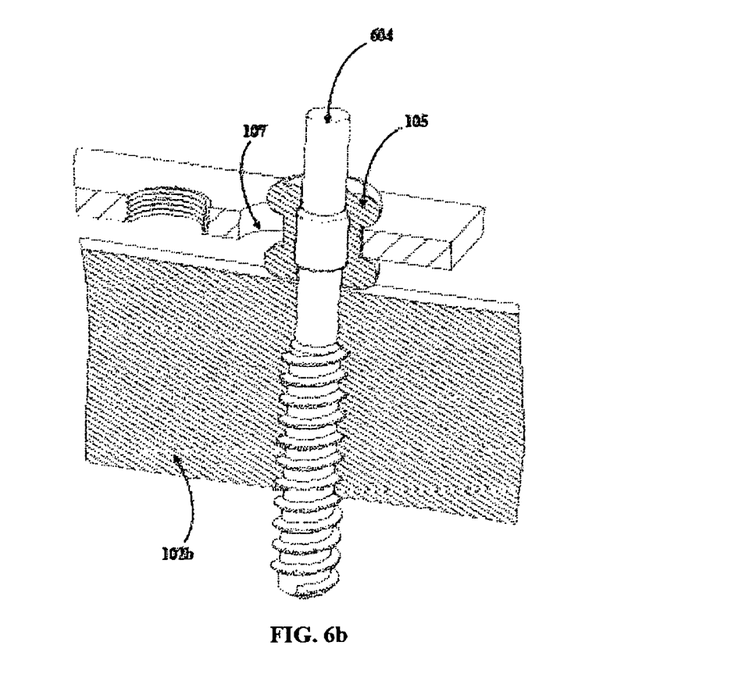
FIG. 6b illustrates a position of the holder that is placed at an elongated hole provided in the locking plate to hold and allow the locking plate to move only in the horizontal direction and to restrict a vertical movement, according to an embodiment herein.

In an embodiment, now referring to FIG. 6a, the holder 105 placed at an elongated hole 107 provided at another side of the locking plate is illustrated. Further, FIG. 6b illustrates a position of the holder that is placed at an elongated hole provided in the locking plate to hold and allow the locking plate to move only in the horizontal direction and to restrict vertical movement, according to an embodiment. In a preferred embodiment, the holder 105 is configured to hold the locking plate 103 above the bone 102 for enabling to make required movement of locking plate 103 in horizontal direction. Further the holder is internally configured to allow a drill bit or tap 604 and lock the drill bit or tap's 604 graduations. In further embodiment, the holder 105 enables to hold the locking plate 103 above the bone 102 and allow the locking plate 103 to move only in the horizontal direction and to restrict the vertical movement.

In an embodiment, the holder 105 is maintained against the bone and a drill bit or tap placed through the holder is used to realign and pull the bone fragments towards the plate and results in plate assisted reduction wherein a plate is used as a template to align bone fragments. The dumbbell 601 maintains a non contact status between the plate and the bone.

In an exemplary embodiment, the holder 105 is provided in a shape like dumbbell 601 with a hole 602 throughout at its centre for allowing a drill bit 604 or tap, and also a slit 603 at outer surface can be provided longitudinally throughout its radius for facilitating press fit and release of the dumbbell 601 for temporarily connecting with the locking plate 103. The diameter of the upper and lower part of the dumbbell 601 is greater than the width of the elongated hole 107 or the diameter of circular locking hole 106. Whereas, the diameter of the middle part of the dumbbell 601 is equal or lesser than the width of the elongated hole 107 or the diameter of circular locking hole 106. In another embodiment, the holder can be in partial dumbbell shape. In another embodiment, the holder can be discrete or in continuation with the external stabilizing mechanism/means.

Figure 7A:
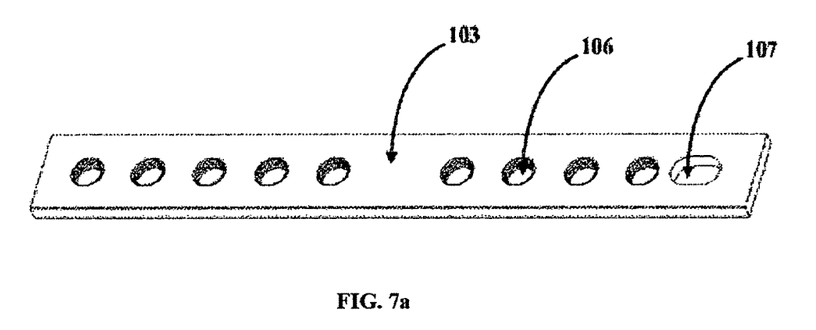
FIG. 7a illustrates a top perspective view of a locking plate according to an embodiment herein.
Figure 7B:
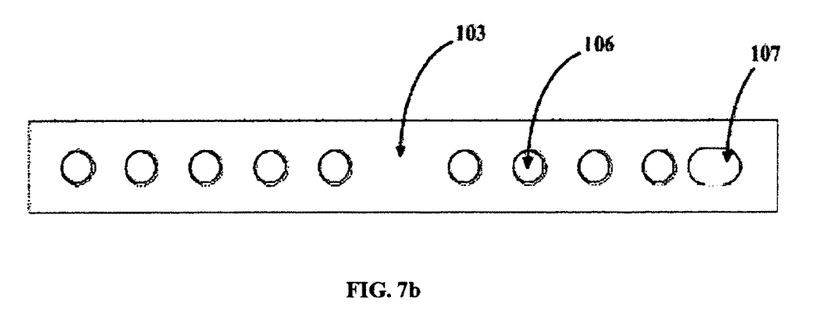
FIG. 7b illustrates a top view of a locking plate according to an embodiment herein.

FIG. 7a illustrates a top perspective view of the locking plate 103 according to an embodiment. FIG. 7b illustrates a top view of a locking plate according to an embodiment. The locking plate includes a plurality of circular locking holes 106 and at least one elongated hole 107.

Accordingly, fastening of the compressing unit 401 can convert a vertical movement of non-locking hemispherical head-screw 411 into the horizontal movement of connecting rod 408 of the compression unit 401, which in turn results in opposite direction movement of another connecting rod 409 of the fixing unit 402, thereby enabling to move the locking plate 103 along with one end of fractured bone 102*a* towards the fractured site 110 thus producing compression between the fractured bones 102.

According to an embodiment, method (s) for locking and compressing fractured bone 102 using a locking plate unit 101 is provided. The exemplary methods are illustrated as a collection of steps in a logical flow representing a sequence of operations that can be implemented with the bone locking unit 101. The order in which the methods are described is not intended to be construed as a limitation, and any order of the described method can be combined in any order to implement the methods, or alternate methods. Additionally, individual steps may be deleted from the methods without departing from the spirit and scope of the subject matter described herein.

According to the present invention method, the locking plate 103 is fastened to one side of fractured bone 102*a* using at least a locking screw 109 for fixing the locking plate 103 and bone 102*a* and keeping the locking plate 103 over bone 102*a* in a non-contact way.

In an embodiment, the graduated drill bit or tap 604 is drilled at predetermined position in the elongated hole 107 provided at one end of the locking plate 103. Thereafter, the holder 105 is introduced in a press-fit manner in the elongated hole 107 over the drill bit or tap's 604 for holding and allowing the locking plate 103 to move only in the horizontal direction and to restrict vertical movement, in effect produces a mobile contoured screw head to the elongated hole 107. Further, the holder 105/dumbbell 601 can be internally configured to hold with the drill bit 604 or tap and to lock the drill bit 604 or tap or is stabilized by external means. The holder can be discrete or may be continuous with the external stabilizing means.

In an embodiment, the fixing unit 402 is placed on the locking plate 103 near the locked screw 109 for fastening the fixing unit 402 with the locking plate 103 using the locking screw 410, wherein the locking screw 410 includes threads matching the threads of locking hole 106. The compression unit 401 is placed on the locking plate 103 near the locked screw 109, wherein the compression unit 401 includes a slope 501 at predetermined variable angle for receiving the hemispherical head screw 411 for fastening the compressing unit 401.

In an embodiment, the box 403 is provided with two racks 404, the gear mechanism 405 in between the two racks 404 and two supporting members 406 to hold the racks 404 with the gear mechanism 405. The compression unit 401 is connected to one rack 404*a* through the connecting rod 408, and the fixing unit 402 is connected to another rack 404*b* through another connecting rod 409. Further, the box 403 can be provided with an upper and lower slot to allow the respective racks 404.

In an embodiment, fastening the screw 411 through the compression unit 401 can result in conversion of a vertical movement of the head-screw 411 into the horizontal movement of the compression unit 401, which in result in backward movement of the connecting rod 408 and rack 404*a*. The backward movement of the rack 404*a* can rotate the gearing mechanism 405, which in turn result in forward movement of another connecting rod 409 and rack 404*b*, wherein the connecting rod 409 is connected with the fixing unit 402. Therefore, the fastening the screw 411 at compression unit 401 enables to move the fixing unit 402 and locking plate 103 along with one end of fractured bone 102*a* towards the fractured site 110 thus producing compression between the fractured bones 102 without contact and friction between locking plate 103 and bone 102, and further required locking screws are fastened in conventional method to complete the construction of locking plate 103 with the bone 102.

In accordance with present invention, the slope and angle of locking hole can be varied and also in higher range, therefore the increased fracture gap can be easily compressed, since the compression unit is independent of the locking plate.

Further, distraction of the fractured bone can also be achieved by positioning the external apparatus and placement of holder in elongated hole reversely. In addition, the distraction and compression between the segmented fractures can also achieved by using a single locking plate. Moreover, the osteotomy distraction and compression can be done at higher magnitude as the compression unit is applied externally.

In an embodiment, buttressing rim can be provided to the locking hole for using non-locking screws to reduce and align the fragmented fractures. Further, the compression can be achieved by choosing non-locking screw of lesser size diameter and undercutting of the locking plate. Moreover, the lagging can also be done all around 360°, wherein the lagging is also achieved by using a holder placed over bone and by over drilling of near cortex, a bone fragment is lagged, wherein the lagged fragments are maintained by a normal or locking screw.

In an embodiment, non-locking screws and buttressing rim with holder in adjacent holes of the locking plate maintains non contact status during alignment of the bone to the plate.

Additionally, providing additional slots for SS wire, K wire at periphery can produce additional temporarily or permanent fixation.

According to an embodiment, bio-absorbable plate can be used as the compression happens above the locking plate. At the same time, the compression and distraction can be achieved without compromising the strength of the locking plate.

According to an embodiment, the thickness of the locking plate can be varied, such as thinner or thicker, or variable thickness within the locking plate can be achieved. Further, the hole spacing in a locking plate length can be reduced, increased, and also can be oriented, staggered, longitudinal and so on. And the angle of locking hole can be varied in their orientation within the locking plate providing multi directional, multiplanar stability thorough a single locking plate.

According to an embodiment, the entire external apparatus, holder and threaded rod matching the pitch of locking hole can be adopted over a zig for biological plating as the zig is anchored to one side of the fracture and the holder can be used at opposite side to produce the external compression and indirect reduction is achieved. Further, the angular misalignment of fractures can be reduced using the present locking plate unit.

In accordance with an embodiment, the orientation of compression slope to the locking plate can be varied to correct any angular deformity present during fracture reduction.

In accordance with an embodiment, the compression unit can be moved by introducing a hemispherical head with internal threads over a threaded rod locked to the locking hole centered beneath the slope. In another embodiment a threaded rod with matching threads to the locking holes is tightened to the locking plate 103 already locked to one fragment of the bone is used as a post locked to a hole as required or adjacent to the elongated hole wherein a holder 105 is positioned over a drill bit or tap at the desired location so as to aid in compression or distraction. Then by "directly" applying the said force mechanically or manually between the threaded post locked to the plate 103 and the drill bit or tap with holder 105 holding the other bone fragment enables the desired movement in the horizontal plane. The threaded rod with matching threads to the locking holes is tightened to the locking plate 103 is used to place the locking plate in optimal position over the bone. As compression and distraction happen using nearby holes located to one side of the fracture and in a non contact way this results with reduced dissection and duration of surgery even without using the external apparatus 104.

According to an embodiment, using the drill bit or tap with holder 105 in an elongated hole 107 and a locking hole 106 of the locking plate 103, compression or distraction can be achieved with a relevant force applied between the threaded rod post and a drill bit or tap mechanically or manually.

In an embodiment, the elongated hole can be configured to lock a locking head screw.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. An orthopedic locking plate unit for connecting and compressing fractured bone without direct contact and friction between the locking plate unit and the fractured bone, wherein the locking plating plate unit comprises:
   a locking plate, an external apparatus and a holder, the locking plate including a plurality of circular locking holes and at least one elongated hole, the at least one elongated hole provided on at least one side of the locking plate, and the holder being placed at the at least one elongated hole;
   wherein said holder is configured to hold the locking plate above the fractured bone for enabling movement of the locking plate in a horizontal direction;
   wherein said holder is in a dumbbell shape and comprises a hole throughout a length of the holder at a centre thereof for receiving a drill bit or tap and a longitudinal slit throughout a radius at an outer surface thereof for facilitating press fit and release; and
   wherein the external apparatus includes a compression unit, a fixing unit and a box.

2. The orthopedic locking plate unit as claimed in claim 1, wherein said box includes two racks, a gear mechanism placed in between the two racks, a plurality of supporting members to hold the two racks with the gear mechanism, a plurality of connecting rods; wherein the compression unit is connected to one of the racks through one of the connecting rods and the fixing unit is connected to the other one of the racks through another one of the connecting rods.

3. The orthopedic locking plate unit as claimed in claim 2, wherein said compression unit includes a slope at predetermined variable angle for receiving a hemispherical head screw for fastening the compression unit with the locking plate to convert a vertical movement of the head screw into horizontal movement of the connecting rod of the compression unit, which in turn results in opposite direction movement of the connecting rod of the fixing unit, thereby enabling the locking plate to move along with one end of the fractured bone towards a fractured site thus producing compression on the fractured bone.

4. The orthopedic locking plate unit as claimed in claim 1, wherein said holder is internally configured to lock graduations of the drill bit or tap, and wherein the holder enables the locking plate to move only in the horizontal direction and restricts vertical movement of the locking plate.

5. The orthopedic locking plate unit as claimed in claim 1, wherein said locking plate unit is made from metal, alloy, polymer, bio-absorbable material or a combination thereof.

6. The orthopedic locking plate unit as claimed in claim 1, wherein said locking plate is provided with a constant or variable thickness across a length thereof.

7. The orthopedic locking plate unit as claimed in claim 1, wherein spacing between said locking holes is variable; wherein said locking holes are orientated at a predetermined angle for providing multi directional and multi planar stability to said locking plate unit.

8. A method for connecting and compressing a fractured bone comprising: providing the locking plate unit as claimed in claim 1,
   fastening the locking plate to one side of the fractured bone using a locking screw for keeping the locking plate over the fractured bone in a non-contact way;
   drilling the drill bit or tap at the at least one elongated hole provided in the locking plate;
   placing the holder in the at least one elongated hole through the drill bit or tap for allowing the locking plate to move only in the horizontal direction, wherein the holder is internally configured to lock the drill bit or tap;
   placing the fixing unit on the locking plate on the one side of the fractured bone with the locking screw;
   fastening the fixing unit to the locking plate using a second locking screw having a plurality of threads matching threads of the locking holes;
   placing the compression unit on the locking plate on the one side of the fractured bone with locking screw;
   providing a box that includes two racks, a gear mechanism placed in between the two racks and two supporting members to hold the racks with the gear mechanism;
   connecting the compression unit to one of the racks through a connecting rod and connecting the fixing unit to the other one of the racks through a second connecting rod, wherein the compression unit includes a slope at a predetermined variable angle for receiving a hemispherical screw head;
   fastening the hemispherical screw head over the slope of the compressing unit to convert vertical movement of the hemispherical screw head into horizontal movement of the connecting rod connected to the compression unit, which in turn results in opposite direction movement of the second connecting rod connected to the fixing unit through the gear mechanism and racks, thereby enabling the locking plate along with one end of the fractured bone to move towards a fractured site;

wherein the fractured bone is connected and compressed without having direct contact or friction with the locking plate.

9. An orthopedic locking plate unit for connecting and compressing a fractured bone without direct contact and friction between the locking plate unit and the fractured bone, the locking plating plate unit comprising a locking plate, a compression unit and a holder, the locking plate including a plurality of circular locking holes and at least one elongated hole, the at least one elongated hole provided on at least one side of the locking plate, and the holder being placed at the at least one elongated hole or at one of the plurality of circular locking holes;

wherein said holder is configured to hold the locking plate above the fractured bone for enabling movement of the locking plate in a horizontal direction;

wherein said holder is in a dumbbell shape and comprises a hole throughout a length of the holder at a centre thereof for receiving a drill bit or tap and a longitudinal slit throughout a radius at an outer surface thereof for facilitating press fit and release; and wherein the compression unit and the holder are configured for temporarily connecting with the locking plate for compression of the fractured bone.

\* \* \* \* \*